US010456045B2

(12) United States Patent
Galea et al.

(10) Patent No.: US 10,456,045 B2
(45) Date of Patent: Oct. 29, 2019

(54) SYSTEM AND METHOD FOR DETERMINING A MEASURE OF THE RESISTANCE OF PERIPHERAL VASCULATURE

(71) Applicants: Vivonics, Inc., Bedford, MA (US); Mayo Foundation For Medical Education and Research, Rochester, MN (US)

(72) Inventors: Anna M. Galea, Stow, MA (US); Jan Stepanek, Scottsdale, AZ (US); Gaurav N. Pradhan, Fountain Hills, AZ (US)

(73) Assignees: Vivonics, Inc., Bedford, MA (US); Mayo Foundation For Medical Education and Research, Rochester, MN (US)

( * ) Notice: Subject to any disclaimer, the term of this patent is extended or adjusted under 35 U.S.C. 154(b) by 0 days.

(21) Appl. No.: 13/950,882

(22) Filed: Jul. 25, 2013

(65) Prior Publication Data
US 2014/0073931 A1   Mar. 13, 2014

Related U.S. Application Data

(60) Provisional application No. 61/676,095, filed on Jul. 26, 2012.

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0059* (2013.01); *A61B 5/021* (2013.01); *A61B 5/7257* (2013.01); *A61B 5/0295* (2013.01)

(58) Field of Classification Search
CPC ... A61B 5/0059; A61B 5/02007; A61B 5/021; A61B 5/0295; A61B 5/7257
See application file for complete search history.

(56) References Cited

U.S. PATENT DOCUMENTS

| | | | |
|---|---|---|---|
| 4,930,517 A | 6/1990 | Cohen et al. | |
| 5,046,504 A * | 9/1991 | Albert | A61B 5/04525 600/509 |

(Continued)

FOREIGN PATENT DOCUMENTS

| | | |
|---|---|---|
| EP | 0330463 A1 | 8/1989 |
| WO | WO 2007/097702 A1 | 8/2007 |

OTHER PUBLICATIONS

Written Opinion of the International Searching Authority for International Application No. PCT/US2013/052197, dated Nov. 20, 2013, (6 pgs. (total)).

(Continued)

*Primary Examiner* — Amelie R Gillman
(74) *Attorney, Agent, or Firm* — Iandiorio Teska & Coleman, LLP

(57) ABSTRACT

A system for determining the resistance of peripheral vasculature including a sensor configured to generate output signals proportional to the amount of blood in the peripheral vasculature over time, and a computer subsystem configured to determine the resistance of the peripheral vasculature in response to the output signals.

5 Claims, 7 Drawing Sheets

(51) Int. Cl.
*A61B 5/021* (2006.01)
*A61B 5/0295* (2006.01)

(56) References Cited

U.S. PATENT DOCUMENTS

| | | | | |
|---|---|---|---|---|
| 6,010,457 A | * | 1/2000 | O'Rourke | A61B 5/0285 600/500 |
| 2006/0238358 A1 | * | 10/2006 | Al-Ali | A61B 5/14552 340/573.1 |
| 2010/0241013 A1 | | 9/2010 | Hatib | |
| 2012/0197142 A1 | * | 8/2012 | Lovejoy | A61B 5/02007 600/507 |
| 2013/0324814 A1 | * | 12/2013 | Maarek | A61B 5/0261 600/324 |

OTHER PUBLICATIONS

Glaser et al., "Physiological Evaluation of the L1/M1 Anti-G Straining Maneuver", <URL:http://www.dtic.mil/dtic/tr/fulltext/u2/a241293.pdf>, Dec. 1990, 15 pgs.
Indu Khurana, "Textbook of Medical Physiology", <URL:http://books.google.com/books?id=M6vviWpZ0LsC&pg=PA313&lpg=PA313&dq=%22peripheral+resistance+unit%22&source=bl&ots=lpllVf8IhT&sig=G-A5BtTQzQDcMntOSx_SOkv384&hl=en&sa=X&ei=OtR7UsqCPMjXyAGMjXyAGM3YDQAQ#v=onepage&q&f=false>, Elsevier, 2006,(3 pgs. (total)).

* cited by examiner

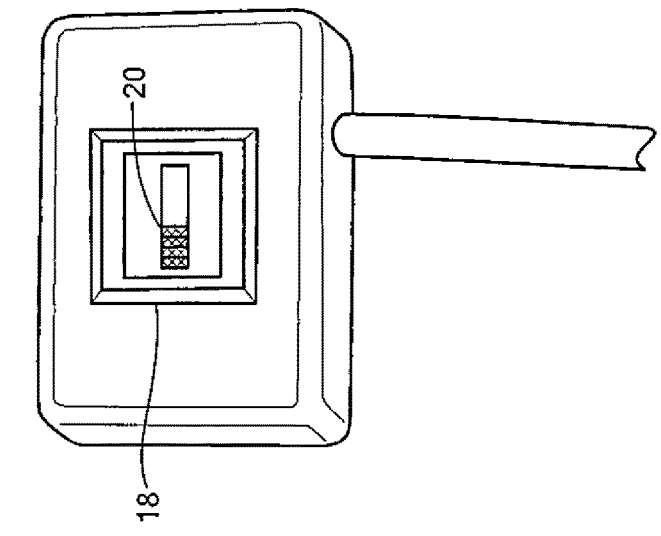
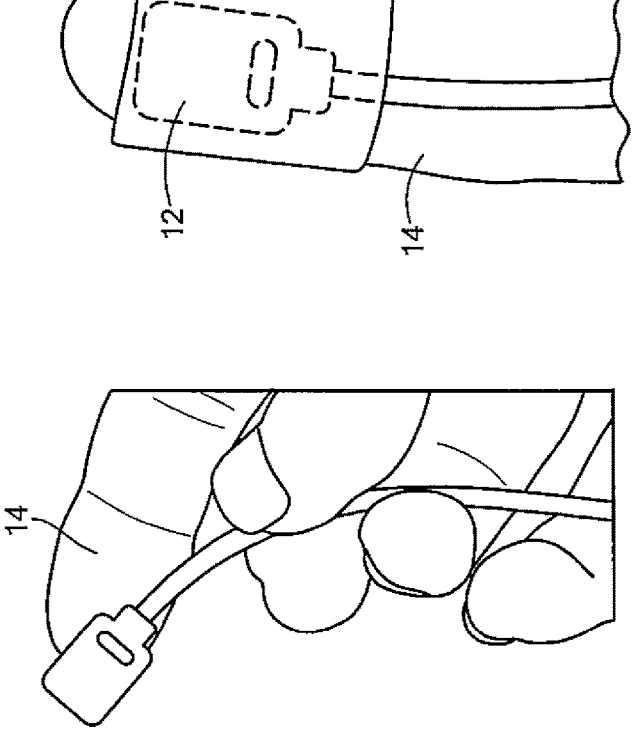
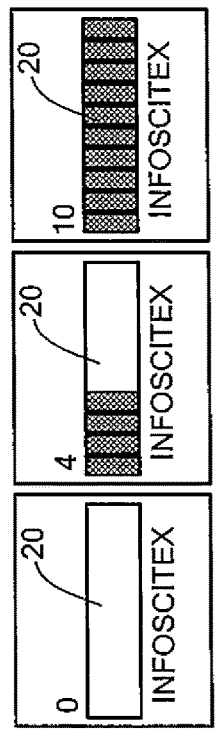
FIG. 4
FIG. 3
FIG. 5
FIG. 2

Transformation
Coefficients: 100

SYSTEM AND METHOD FOR DETERMINING A MEASURE OF THE RESISTANCE OF PERIPHERAL VASCULATURE

RELATED APPLICATIONS

This application hereby claims the benefit of and priority to U.S. Provisional Application Ser. No. 61/676,095, filed on Jul. 26, 2012 under 35 U.S.C. §§ 119, 120, 363, 365, and 37 C.F.R. § 1.55 and § 1.78, incorporated by reference herein.

GOVERNMENT RIGHTS

This invention was made with U.S. Government support under Contract No. N68335-08-C-0141 and N68335-10-C-0079, awarded by NAVAIR. The Government may have certain rights in certain aspects of the subject invention.

FIELD OF THE INVENTION

This invention relates to a system and method for determining a measure of the resistance of the peripheral vasculature.

BACKGROUND OF THE INVENTION

Centrifuge training is a necessary part of flight training for pilots expected to encounter high gravitational force ("G-force" or "G") flight conditions. The anti-G straining maneuver (AGSM) may be an important part of protection against Gravity-induced Loss of Consciousness (G-LOC). However, conventional training for the AGSM is qualitative at best. A method to measure and provide feedback on the quality of the AGSM would help trainees learn the proper application of AGSM technique.

The AGSM typically includes both straining the lower body musculature and breathing in a specific manner to increase the pressure in the thoracic cavity. When performed properly, the AGSM serves to increase the resistance of the peripheral vasculature so that blood will preferentially flow to the brain.

Conventional devices are known which utilize a pressure wave in the wrist (radial tonometry) and provide a value for an Augmentation Index which is a measure of the resistance of the peripheral vasculature. However, radial tonometry is a delicate measurement that requires the sensor be placed in exactly the right location and the subject cannot move during the test.

Thus, there is need for a robust and easy to use system and method which can measure the resistance of peripheral vasculature to provide, inter alia, feedback to the quality of the AGSM technique. This method may also be useful for medical applications in which the resistance of the peripheral vasculature is important, such as hypovolemia, shock, and the like.

SUMMARY OF THE INVENTION

In one aspect, a system for determining the resistance of peripheral vasculature is featured. The system includes a sensor configured to generate output signals proportional to the amount of blood in the peripheral vasculature over time of a predetermined body part and a computer subsystem configured to determine the resistance of the peripheral vasculature in response to the output signals.

In one embodiment, the sensor may be configured to emit light in the near-infrared or infrared spectra to peripheral vasculature in the predetermined body part and measure the light absorbed by the peripheral vasculature to generate the output signal proportional to the amount of blood in the peripheral vasculature over time. The sensor may be configured to measure the pressure in the predetermined body part by generating the output signals proportional to the amount of blood in the peripheral vasculature. The predetermined body part may include a finger, thumb, hand, arm, abdomen, foot, or a body part directly associated with the peripheral vasculature. The system may include a display device coupled to the computer system configured to display the resistance of the peripheral vasculature. The computer subsystem may include an algorithm configured to calculate the resistance of the peripheral vasculature. The algorithm may be configured to round the calculated resistance of peripheral vasculature to an integer between 0 and 10. The display device may be configured to display an integer rounded from the calculated value to provide a digit indication of the measured resistance to the peripheral vasculature. The display device may be configured to display the resistance of the peripheral vasculature as a bar graph. The algorithm may be configured to calculate the resistance of the peripheral vasculature using a transfer function. The transfer function may be configured to calculate the resistance of the peripheral vasculature using time content of the output signals. The algorithm may be configured to calculate the resistance of the peripheral vasculature using the frequency content of the output signals. The algorithm may include a Fourier transform. The resistance of the peripheral vasculature may include an anti-G straining maneuver (AGSM) index.

In another aspect, a method for determining a measure of the resistance of peripheral vasculature is featured. The method includes generating and monitoring output signals proportional to the amount of blood in the peripheral vasculature of a predetermined body part over time and determining the resistance of the peripheral vasculature in response to the output signals.

In one embodiment, the output signals may be generated by emitting light in near red or infrared spectra to peripheral vasculature in a predetermined body part and measuring the light absorbed by the peripheral vasculature. The output signals may be generated by measuring the pressure in the predetermined body part. The method may include the step of displaying the resistance of the peripheral vasculature. The method may include the step of displaying the resistance of the peripheral vasculature as an integer ranging from 0 to 10. The method may include the step of displaying the resistance of the peripheral vasculature as a bar graph. The resistance of the peripheral vasculature may include calculating the resistance of the peripheral vasculature using a transfer function. Calculating may include using the time content of the output signals. Calculating may include using the frequency content of the output signals.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 2 is a three-dimensional view showing in further detail one example of the sensor shown in FIG. 1;

FIG. 3 is a three-dimensional view showing the sensor shown in FIGS. 1-2 in place on a finger;

FIG. 4 is a three-dimensional view showing in further detail one example of the display device shown in FIG. 1;

FIG. 5 shows examples of bar graphs and integers output by the display device shown in FIGS. 1 and 4 which may be used to represent the measure of the resistance of the peripheral vasculature of one embodiment of this invention;

FIG. 10 shows examples of transformation coefficients which may be utilized by the algorithm shown in FIG. 9 to calculate the resistance of the peripheral vasculature.

DETAILED DESCRIPTION OF THE INVENTION

Figure 1:
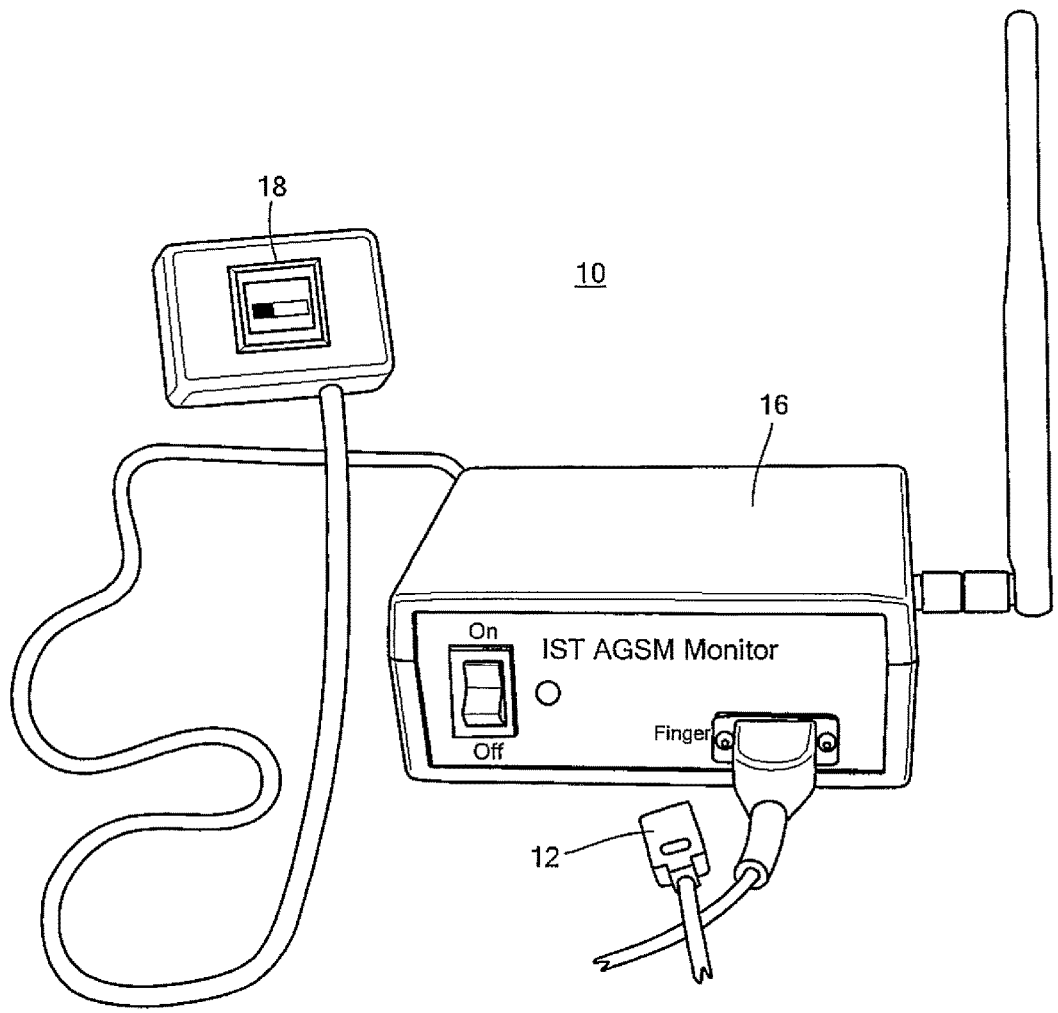
FIG. 1 is a three-dimensional view showing the primary components of one embodiment of the system and method for measuring the resistance of the peripheral vasculature of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one embodiment of system 10 and the method thereof for determining a measure of the resistance of peripheral vasculature. System 10 includes sensor 12, e.g., a near infra-red (NIR) sensor, or a similar type sensor, such as a sensor used in pulse oximetry, or a pressure sensor or similar type sensor. Sensor 12 is configured to generate output signals proportional to the amount of blood in the peripheral vasculature over time. In one example, when sensor 12 is configured as a NIR sensor, sensor 12 emits NIR spectra to the peripheral vasculature of a predetermined body part, measures the light absorbed by the peripheral vasculature of the predetermined body part, and generates output signals proportional to the amount of blood in the peripheral vasculature over time. In another design, when sensor 12 is configured as a pressure sensor, sensor 12 measures the pressure in the predetermined body part to generate output signals proportional to the amount of blood in the peripheral vasculature over time. In one example, the predetermined body part may be the finger of a subject or trainee, e.g., finger 14, FIG. 2. FIG. 3 shows one example of sensor 12 in place on finger 14. In other examples, sensor 12 may be placed on another part of the finger as shown in FIG. 3, the thumb, hand, arm, abdomen, foot, or other body part directly associated with the peripheral vasculature.

System 10, FIG. 1, also includes computer subsystem 16 which determines the resistance of the peripheral vasculature in response to the output signals generated by sensor 12. In one example, computer subsystem 16 may use an algorithm to calculate the resistance of the peripheral vasculature, discussed in further detail below. System 10 also preferably includes display device 18, e.g., an LCD display as shown, or a computer monitor, PDA, or similar type display device, which displays the calculated resistance of the peripheral vasculature. The calculated resistance of the peripheral vasculature may also include an AGSM index.

Figure 6:
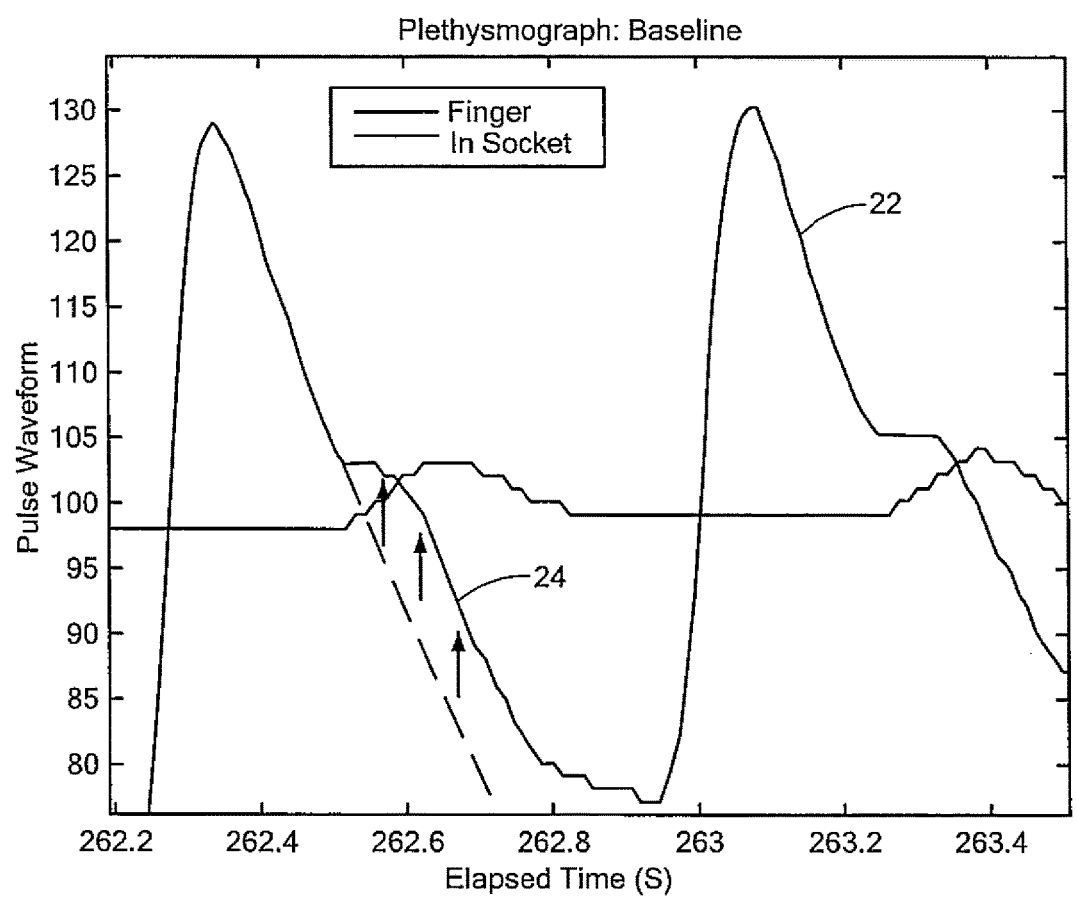
FIG. 6 shows one example of a graph which may be used to represent the measure of the resistance of the peripheral vasculature of the system shown in FIG. 1.

In one example, the algorithm utilized by computer subsystem 16 rounds the calculated resistance of the peripheral vasculature to an integer between 0 and 10. In this example, display device 18, shown in greater detail in FIG. 4, displays the calculated resistance of the peripheral vasculature as an integer value and bar graph 20. FIG. 5 shows in further detail examples of the output of display device 18 where the calculated resistance of the peripheral vasculature is displayed as bar graph 20 and the rounded integer value 0, 4, and 10 is displayed as shown. Plot 22, FIG. 6, shows another example of the calculated resistance of the peripheral vasculature generated by system 10 and the method thereof which may be displayed on a monitor. The amount of augmentation due to the resistance of the peripheral vasculature is indicated at 24.

The result is system 10 efficiently and effectively measures the resistance of the peripheral vasculature using sensor 12 which may be easily attached to the finger or other body part. System 10 allows the user to move, does not need to be exactly located, and is not as delicate a conventional radial tonometry. The bar graph and integer display of the calculated resistance of the peripheral vasculature are easy to read and understand.

Figure 7:
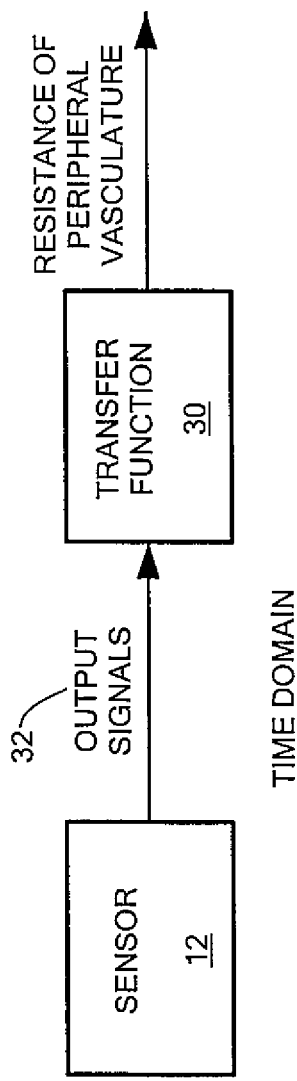
FIG. 7 is a block diagram showing one example of a transfer function which may be used by the computer subsystem shown in FIG. 1 to calculate the resistance of the peripheral vasculature.

In one embodiment, computer system 16, FIG. 1, may use an algorithm to calculate the resistance of the peripheral vasculature may use a transfer function. In one example, transfer function 30, FIG. 7, responsive to output signals 32 from sensor 12, FIG. 1, may be used by the algorithm. In this example, the algorithm uses the time content, or time domain, of output signals 32 to calculate the resistance of peripheral vasculature. In another example, the algorithm may use frequency content, or frequency domain, of output signals 32, FIG. 8, from sensor 12, FIG. 1. In this example, Fourier transform 34, FIG. 8, generates Fourier coefficients 36. Transfer function 38 then utilizes Fourier coefficients 36 to generate the resistance of the peripheral vasculature. In this example, the algorithm is a transfer function between Fourier coefficients 36 and the value of the peripheral vasculature. Preferably, in one example, only the first eight positive values of Fourier transform 34 are used. The transfer function is also preferably linear. The algorithm preferably rounds the integer value to a value between 0 and 10, which may be displayed as shown in FIGS. 4 and 5, discussed above. If the calculated resistance of the peripheral vasculature is less than 0 it is rounded to 0, if it is greater than 10 it is rounded to 10. Otherwise, the value is rounded up to the nearest integer.

Figure 8:
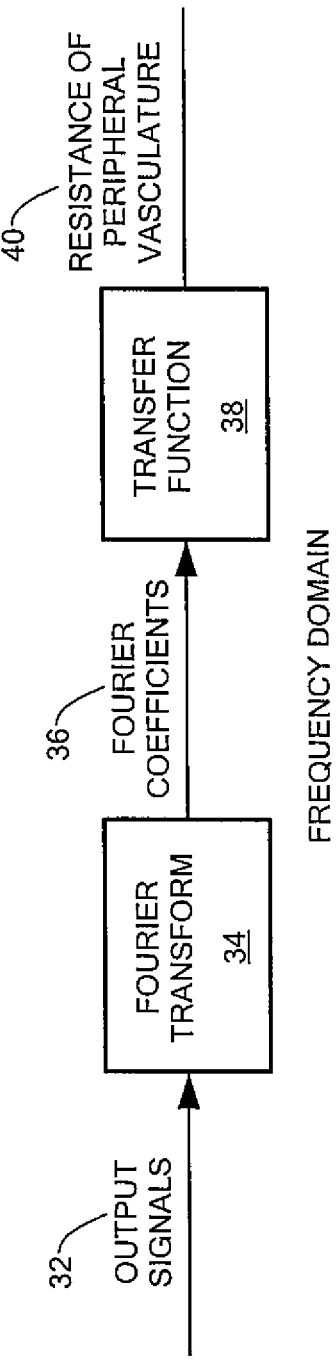
FIG. 8 is a block diagram showing one example of a Fourier Transform and transfer function which may be used by the computer subsystem shown in FIG. 1 to calculate the resistance of the peripheral vasculature.
Figure 9:
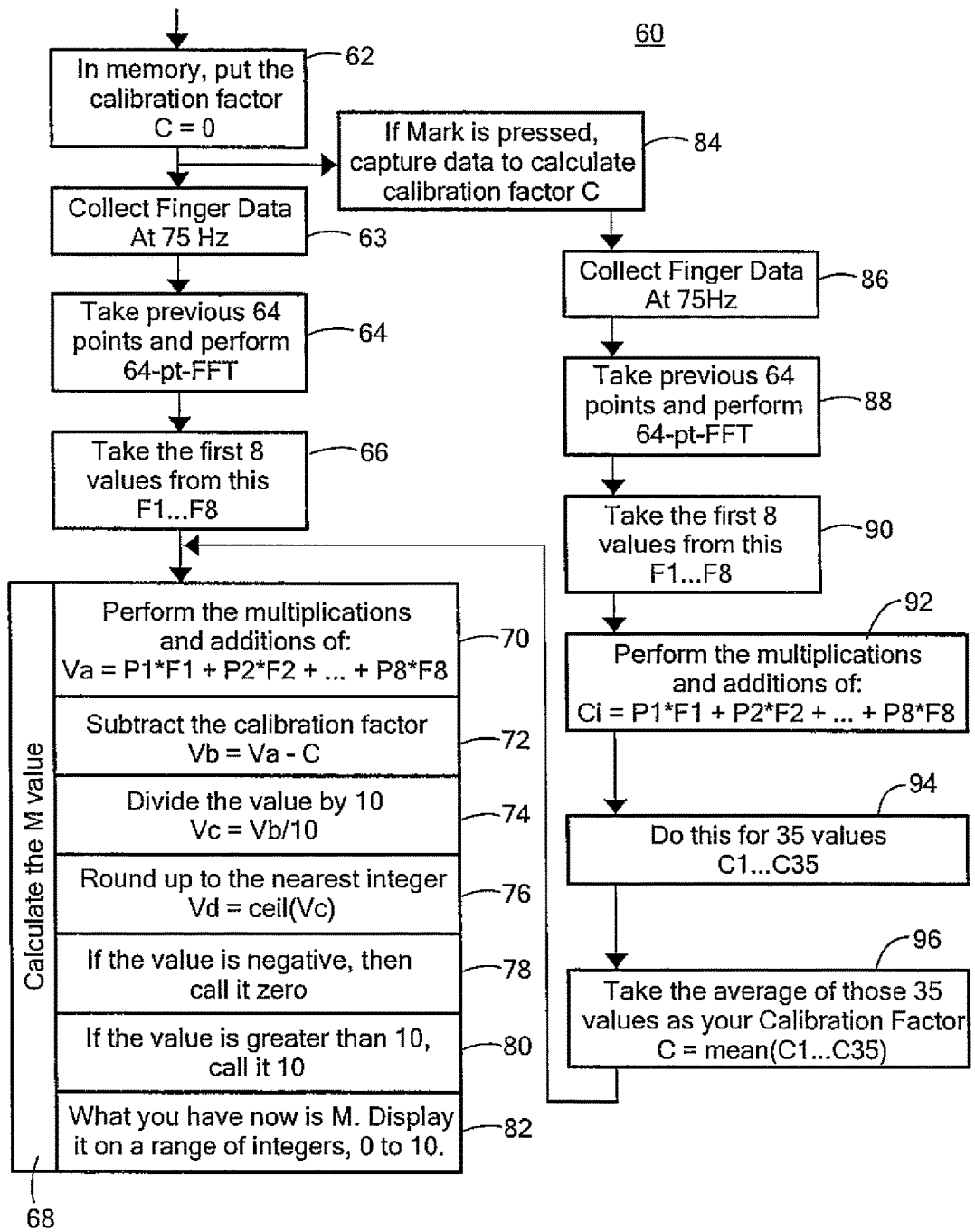
FIG. 9 is a flow chart showing one example of an algorithm which may be used by the computer subsystem shown in FIG. 1 to calculate the resistance of the peripheral vasculature.

FIG. 9 shows a flow chart of one example of the method for determining the resistance of peripheral vasculature using algorithm 60 which may utilize Fourier transform 34, FIG. 8, and transfer function 38 to calculate the resistance to the peripheral vasculature, The method includes putting the calibration factor into memory, step 62. Finger data is then collected, step 61. The previous 64 points are taken and a 64 point fast Fourier transform is performed, step 64. The first eight values from step 64 are then taken, step 66, The measured resistance of the peripheral vasculature M values are then calculated, step 68. Step 68 may include performing multiplications and additions of the equation Va=P1*F1+ P2*F2+ . . . +P8*F8, step 70, subtracting the calibration factor, step 72, dividing the value calculated in step 72 by 10, step 74, and rounding-up to the nearest integer value, step 76. If the value is negative it is set to zero, step 78. If the value is greater than ten, it is set to 10, step 80. The measured peripheral vasculature, M, is displayed as a range of integers from 0 to 10, step 82. The method may also include if Mark is pressed, data is captured to calculate the calibration factor, step 84. Finger data is collected, step 86. The previous 64 points of data are then taken and a 64 point fast Fourier transform is performed, step 88. The first eight values from the FFT are then taken, step 90. Multiplications and additions of the equation Ci=P1*F1+P2*F2+ . . . +P8*F8 are then performed, step 92. This is then done for thirty-five values of C1 . . . C35, step 94. The average of the thirty-five values is the calibration factor, step 96. The values from step 96 may then be provided to step 68.

Figure 11:
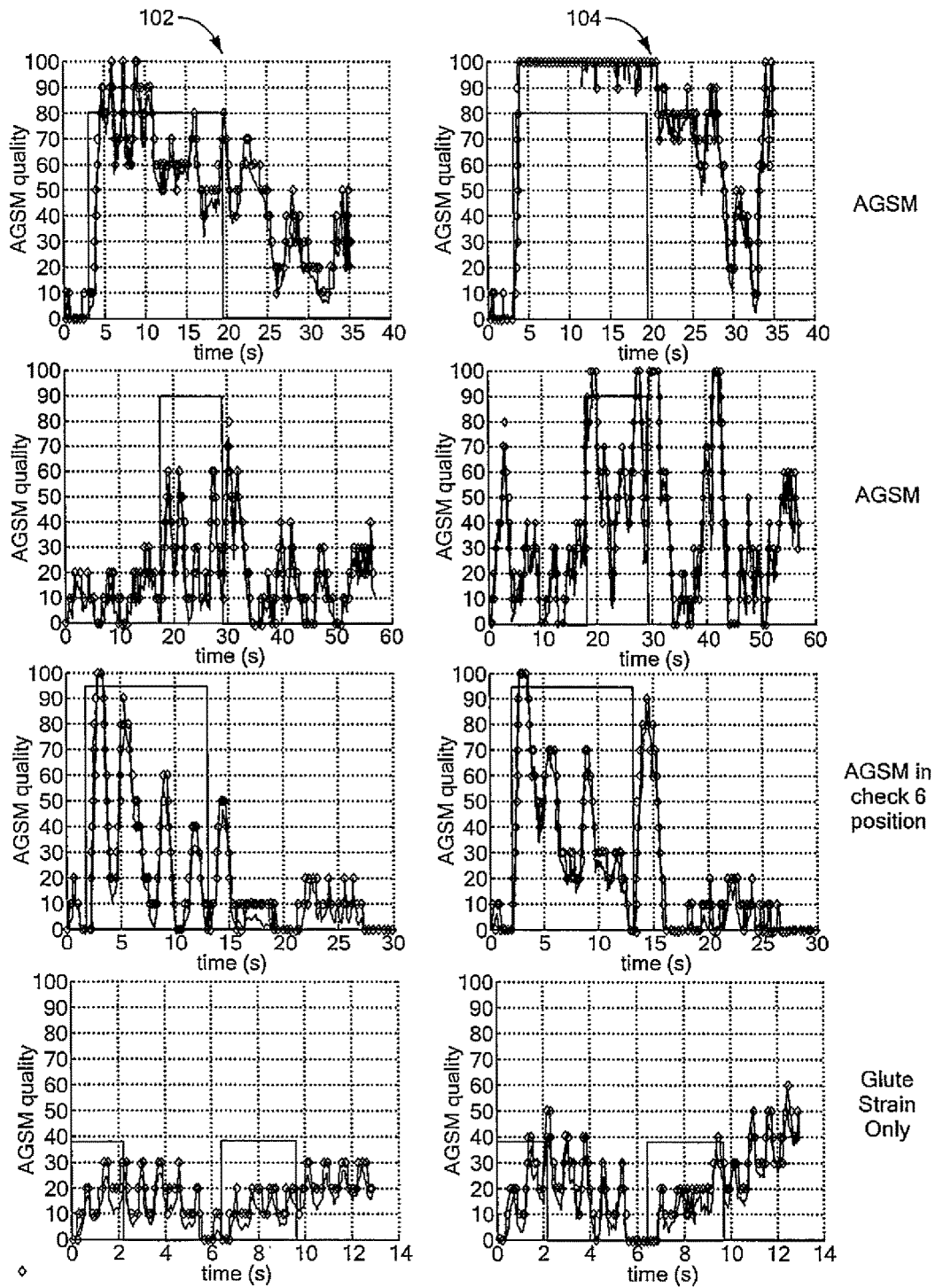
FIG. 11 depicts plots of exemplary results using from an 8-pt algorithm and a 64-pt algorithm which may be used by the computer subsystem shown in FIG. 1.

FIG. 10 shows exemplary transformation coefficients 99. FIG. 11 shows examples of sample results for measured resistance of the peripheral vasculature using an 8-pt algorithm, indicated at 102 and the corresponding 64-pt algorithm, indicated at 104.

System 10 may make a positive impact on G-training, or ASGM, including, inter alia, providing real-time feedback to trainees, help trainees adjust their strains appropriately, screening trainees before entering the centrifuge, reducing the number of trainees who do not pass G tests. The result is system 10 and method thereof for measuring the resistance of the peripheral vasculature may save considerable time and money, and provide a method for personnel who need to stay qualified, a method of practicing at home, and verify trainees are practicing properly.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A method for determining a measure of the resistance of peripheral vasculature, the method comprising:
    using a sensor adapted to be placed on a predetermined body part associated with peripheral vasculature to emit light in the near-infrared or infrared spectra to the peripheral vasculature in the predetermined body part and measure light absorbed by the peripheral vasculature to generate output signals proportional to an amount of blood in the peripheral vasculature of the predetermined body part over time;
    using a computer subsystem to determine, in response to the output signals proportional to an amount of blood in the peripheral vasculature of a predetermined body part over time, the resistance of the peripheral vasculature using frequency content of the output signals; and
    using the determined resistance of the peripheral vasculature to provide feedback regarding an anti-gravity straining maneuver.

2. The method of claim 1 further including displaying the resistance of the peripheral vasculature.

3. The method of claim 2 wherein displaying includes displaying the resistance of the peripheral vasculature as an integer ranging from 0 to 10.

4. The method of claim 2 wherein displaying includes displaying the resistance of the peripheral vasculature as a bar graph.

5. The method of claim 1 in which determining the resistance of the peripheral vasculature includes calculating the resistance of the peripheral vasculature using a transfer function.

* * * * *

UNITED STATES PATENT AND TRADEMARK OFFICE
CERTIFICATE OF CORRECTION

PATENT NO.         : 10,456,045 B2
APPLICATION NO.    : 13/950882
DATED              : October 29, 2019
INVENTOR(S)        : Galea et al.

Page 1 of 1

It is certified that error appears in the above-identified patent and that said Letters Patent is hereby corrected as shown below:

In the Specification

Column 1, Lines 15-18 reads "This invention was made with U.S. Government support under Contract No. N68335-08-C-0141 and N68335-10-C-0079, awarded by NAVAIR. The Government may have certain rights in certain aspects of the subject invention." Should read "This invention was made with U.S. Government support under Contract No. N68335-08-C-0141 and N68335-10-C-0079, awarded by NAVAIR. The Government has certain rights in the invention."

Signed and Sealed this
Fourth Day of February, 2020

Andrei Iancu
*Director of the United States Patent and Trademark Office*